US00PP31728P2

(12) United States Plant Patent
Knosher

(10) Patent No.: US PP31,728 P2
(45) Date of Patent: May 5, 2020

(54) ***GOMPHRENA* PLANT NAMED 'PAST0517E'**

(50) Latin Name: *Gomphrena pulchella*
Varietal Denomination: PAST0517E

(71) Applicant: Ball Horticultural Company, West Chicago, IL (US)

(72) Inventor: Lynne Knosher, St. Charles, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 16/501,923

(22) Filed: Jul. 3, 2019

Related U.S. Application Data

(60) Provisional application No. 62/917,033, filed on Nov. 16, 2018.

(51) Int. Cl.
*A01H 5/02* (2018.01)
*A01H 6/14* (2018.01)

(52) U.S. Cl.
USPC ..... Plt./263.1
CPC ..... *A01H 6/14* (2018.05)

(58) Field of Classification Search
USPC ..... Plt./263.1
CPC ..... A01H 5/02; A01H 6/00; A01H 6/30
See application file for complete search history.

*Primary Examiner* — Keith O. Robinson
(74) *Attorney, Agent, or Firm* — Audrey Charles

(57) ABSTRACT

A new and distinct cultivar of *Gomphrena* plant named 'PAST0517E', characterized by its red-purple colored inflorescences, dark green-colored foliage, and vigorous, upright-mounded growth habit, is disclosed.

1 Drawing Sheet

Latin name of genus and species of plant claimed: *Gomphrena pulchella.*
Variety denomination: 'PAST0517E'.

BACKGROUND OF THE INVENTION

The present invention relates to a new and distinct cultivar of *Gomphrena* plant botanically known as *Gomphrena pulchella* and hereinafter referred to by the cultivar name 'PAST0517E'.

The new cultivar originated in a controlled breeding program in Elburn, Ill. during September 2013. The objective of the breeding program was the development of *Gomphrena* cultivars with continuous flowering and a mounded growth habit.

The new *Gomphrena* cultivar is the result of open-pollination of a group of proprietary *Gomphrena pulchella* breeding selections not coded, not patented, characterized by red-purple colored inflorescences, medium green-colored foliage, and vigorous, mounded growth habit. Seed was harvested from all plants and sown in the field. The new cultivar was discovered and selected as a single flowering plant within the progeny of the above stated open-pollination during July 2014 in a controlled environment in Santa Paula, Calif.

Asexual reproduction of the new cultivar by terminal stem cuttings since July 2014 in West Chicago, Ill. and Alajuela, Costa Rica has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'PAST0517E' as a new and distinct cultivar of *Gomphrena* plant:

1. Red-purple colored inflorescences;
2. Dark green-colored foliage; and
3. Vigorous, upright-mounded growth habit.

Plants of the new cultivar differ from plants of the possible female and male parents primarily in having a lighter shade of inflorescence color, a shorter plant height and more branches per plant.

Of the many commercially available *Gomphrena* cultivars, the most similar in comparison to the new cultivar is 'Cosmic Flare', U.S. Plant Pat. No. 28,411. However, in comparison, plants of the new cultivar differ from plants of 'Cosmic Flare' in at least the following characteristics:

1. Plants of the new cultivar have darker green-colored leaves than plants of 'Cosmic Flare'; and
2. Plants of the new cultivar have wider inflorescences than plants of 'Cosmic Flare'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'PAST0517E'. The plants were grown in 6-inch pots for approximately 10 weeks in a greenhouse in West Chicago, Ill.

DETAILED BOTANICAL DESCRIPTION

Figure 1:
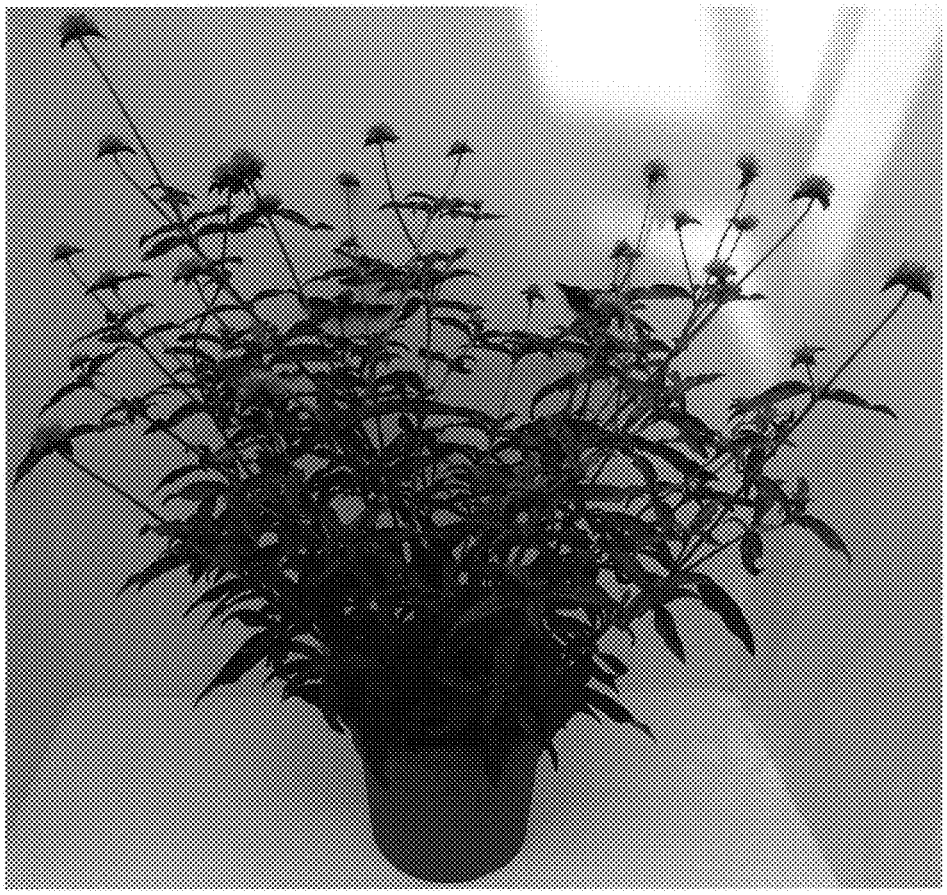
FIG. 1 illustrates a side view of the overall growth and flowering habit of 'PAST0517E'.
Figure 2:
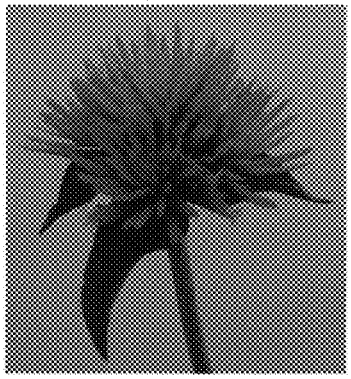
FIG. 2 illustrates a close-up view of an individual inflorescence of 'PAST0517E'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in May 2019 under natural light conditions in West Chicago, Ill.

The following descriptions and measurements describe approximately 4-month old plants produced from cuttings from stock plants and grown in a glass-covered greenhouse under conditions comparable to those used in commercial practice. The plants were grown in West Chicago, Ill. in 6-inch pots for approximately 10 weeks utilizing a soilless growth medium. Greenhouse temperatures were maintained at approximately 67° F. to 72° F. (19° C. to 22° C.) during the day and approximately 65° F. to 68° F. (18° C. to 20° C.) during the night. Supplemental lighting was used. Measurements and numerical values represent averages of typical plants.

Botanical classification: *Gomphrena pulchella* 'PAST0517E'.

Parentage:

*Female parent.*—Proprietary *Gomphrena pulchella* breeding selection not coded, not patented.

*Male parent.*—Proprietary *Gomphrena pulchella* breeding selection not coded, not patented.

Propagation:

*Type cutting.*—Terminal stem.

*Time to initiate roots.*—Approximately 12 to 14 days.

*Time to produce a rooted cutting.*—Approximately 5 to 6 weeks.

*Root description.*—Fibrous, fine.

*Rooting habit.*—Freely branching, moderate density.

Plant description:

*Commercial crop time.*—Approximately 6 to 8 weeks from a rooted cutting to finish in a 15 cm pot.

*Growth habit and general appearance.*—Annual, vigorous, upright-mounded.

*Size.*—Height from soil level to top of plant plane: Approximately 55.0 cm. Width: Approximately 65.0 cm.

*Branching habit.*—Freely branching, pinching enhances basal branching. Quantity of lateral branches per plant: Approximately 14.

*Branch.*—Shape: Rounded. Strength: Strong. Length: Approximately 46.0 cm. Diameter: Approximately 4.0 mm to 5.0 mm. Length of central internode: Approximately 7.0 cm. Texture: Densely pubescent, strigose. Color of young stem: 146B with an overlay of 187C at nodes. Color of mature stem: 146A with an overlay of 187B at nodes.

Foliage description:

*General description.*—Quantity of leaves per lateral branch: Approximately 8. Fragrance: None detected. Form: Simple. Arrangement: Opposite.

*Leaves.*—Aspect: Perpendicular to stem. Shape: Lanceolate, keeled. Margin: Entire. Apex: Acute. Base: Sessile. Venation pattern: Pinnate. Length of mature leaf: Approximately 10.5 cm. Width of mature leaf: Approximately 2.0 cm. Texture of upper surface: Moderately pubescent. Texture of lower surface: Densely pubescent, strigose. Color of upper surface of young foliage: NN137A and midvein of 146C other venation indistinguishable from laminae. Color of lower surface of young and mature foliage: Closest to 147B. Color of upper surface of mature foliage: NN137A with 139A and midvein of 146C other venation indistinguishable from laminae.

Flowering description:

*Flowering habit.*—'PAST0517E' is freely flowering under outdoor growing conditions with substantially continuous blooming from spring through autumn.

*Lastingness of individual inflorescence on the plant.*—Approximately 30 days.

Inflorescence description:

*General description.*—Type: Clover-like, papery-like heads, persistent. Quantity per plant: Approximately 37. Fragrance: None detected. Aspect: Facing upward or outward. Height: Approximately 1.8 cm. Width: Approximately 3.0 cm. Quantity of fully open flowers per inflorescence: Approximately 120.

*Peduncle.*—Strength: Strong. Shape: Round. Aspect: Erect to acute angle to stem. Length: Approximately 10.0 cm. Diameter: Approximately 2.0 mm. Texture: Densely pubescent, strigose. Color: 146A.

Flower description:

*General description.*—Type: Tubular, sessile with a five-parted perianth in a single whorl subtended by two bracts.

*Bud just before opening.*—Shape: Oblong. Length: Approximately 6.0 mm. Diameter: Approximately 1.0 mm. Color: N78C.

*Perianth segments.*—Quantity: 5. Shape: Lanceolate. Margin: Entire. Apex: Acute. Base: Truncate. Length: Approximately 1.0 cm. Width: Approximately 1.0 mm. Texture: Glabrous with sericeous base, papery-like. Color of inner surface: N78C with NN155D at base. Color of outer surface: N78A to N78B with NN155D at base.

*Bracts.*—Quantity per flower: 2 per flower. Shape: Ovate, keeled. Length: Approximately 5.0 mm. Width: Approximately 1.0 mm. Texture of upper and lower surfaces: Glabrous, translucent. Color of upper and lower surfaces: NN155D and N78B.

*Reproductive organs.*—Androecium: Stamen quantity and arrangement: Filaments united into a cylindrical tube with five acute tips, tube encases the gynoecium. Filament length: Approximately 1.1 mm. Filament tube width: Approximately 1.5 mm. Color of outer and inner surfaces of filament tube: Tips of 14A, top of tube potion of N78B transitioning though NN155D to base of 146C. Anther shape: Oblong, dosifixed to filament tip. Anther length: Approximately 3.0 mm. Anther color: 14A. Pollen amount: Sparse. Pollen color: 14B. Gynoecium: Pistil quantity: 1 per flower. Pistil length: Approximately 3.0 mm. Stigma shape: Bi-parted. Stigma length: Approximately 2.0 mm. Stigma color: 145D, translucent. Style length: Less than 1.0 mm. Style color: 146D. Ovary diameter: Less than 1.0 mm. Ovary color: 146D.

Seed and fruit production: Neither seed nor fruit production has been observed.

Disease and pest resistance: Resistance to pathogens and pests common to *Gomphrena* has not been observed.

What is claimed is:

1. A new and distinct cultivar of *Gomphrena* plant named 'PAST0517E', substantially as herein illustrated and described.

* * * * *